United States Patent [19]

Irion

[11] Patent Number: 5,166,787
[45] Date of Patent: Nov. 24, 1992

[54] ENDOSCOPE HAVING PROVISION FOR REPOSITIONING A VIDEO SENSOR TO A LOCATION WHICH DOES NOT PROVIDE THE SAME CROSS-SECTIONALLY VIEWED RELATIONSHIP WITH THE DISTAL END

[75] Inventor: Klaus Irion, Emmingen-Liptingen, Fed. Rep. of Germany

[73] Assignee: Karl Storz GmbH & Co., Fed. Rep. of Germany

[21] Appl. No.: 656,075

[22] PCT Filed: Jun. 28, 1990

[86] PCT No.: PCT/DE90/00486
§ 371 Date: Feb. 28, 1991
§ 102(e) Date: Feb. 28, 1991

[87] PCT Pub. No.: WO91/00049
PCT Pub. Date: Jan. 10, 1991

[30] Foreign Application Priority Data
Jun. 28, 1989 [DE] Fed. Rep. of Germany ....... 3921233

[51] Int. Cl.⁵ .............................................. H04N 7/18
[52] U.S. Cl. ....................................... 358/98; 358/100
[58] Field of Search ................. 358/98, 100, 229, 209, 358/225, 93; 128/4-6

[56] References Cited

U.S. PATENT DOCUMENTS

| 4,253,447 | 3/1981 | Moore et al. . |
| 4,261,344 | 4/1981 | Moore et al. . |
| 4,905,670 | 3/1990 | Adair ................................ 358/98 X |
| 4,926,257 | 5/1990 | Miyazaki ............................ 358/98 |

FOREIGN PATENT DOCUMENTS

| 2529026 | 2/1986 | Fed. Rep. of Germany . |
| 3720624 | 1/1989 | Fed. Rep. of Germany . |

Primary Examiner—Victor R. Kostak
Attorney, Agent, or Firm—Evenson, Wands, Edwards, Lenahan & McKeown

[57] ABSTRACT

An endoscope has a video device arranged at the distal end of the endoscope shaft. The video device is connected by means of a transmission system to a supply unit arranged at the proximal end of the endoscope shaft. The video device is provided with a lens for imaging an object field and an illumination unit. The lens and the image recorder are combined into a video unit which is held in such a movable manner at the endoscope shaft that the outer contour of the cross-section of the video unit lays essentially within the outer contour of the cross-section of the distal end of the endoscope shaft when being introduced into the cavity to be examined. After termination of the introduction procedure, the video unit can be moved in relation to the distal end of the endoscopic shaft beyond the outer contour of the cross-section and/or longitudinal section.

52 Claims, 6 Drawing Sheets

ENDOSCOPE HAVING PROVISION FOR REPOSITIONING A VIDEO SENSOR TO A LOCATION WHICH DOES NOT PROVIDE THE SAME CROSS-SECTIONALLY VIEWED RELATIONSHIP WITH THE DISTAL END

BACKGROUND AND SUMMARY OF THE INVENTION

The present invention relates to an endoscope with a video device, which is arranged at the distal end of an endoscope shaft and is connected by means of a transmission system to a supply unit arranged at the proximal end thereof and is provided with a lens, which images an object field illuminated by an illumination unit onto an image recorder.

Endoscopes serve to inspect cavities for the purpose of examination and/or manipulation and have found a great number of applications in technology and medicine.

Conventional endoscope have a so called image forwarder arranged at the distal end, which "forwards" the image produced by the lens from the distal end to the proximal end, where it is examined by means of an eyepiece. In "rigid" endoscopes, the image forwarder is composed of so-called relay lens sets and in flexible endoscopes of fiber bundles.

Small-sized video image recorders, as by way of illustration CCD chips, have been available for some time. For this reason, it has often been proposed instead of using an image forwarder, to provide an image recorder in the image plane of the lens at the distal end, which is connected via a transmission system to a supply unit provided at the proximal end. See for example U.S. Pat. Nos. 4,253,447 and 4,261,344, in which an "upright" semiconductor image recorder, i.e. an image recorder standing at a 90° angle to the axis of the endoscope, is arranged in the image plane of the lens provided at the distal end.

With this kind of an arrangement of the image-recorder chip, however, problems occur, particularly in medical endoscopes, as presently image-recording chips are relatively large compared to the size of medical endoscopes. The size of the image-recording chip is especially inconvenient in endoscopes which are employed not only for examination of a cavity, but also for manipulation therein, and have for this purpose leading from the distal end to the proximal end a main duct, into which, by way of illustration, scissors, tweezers, etc. can be inserted. In order that the image, recording chip, not limit too severely the lumen available for the main duct, it has been suggested, by way of illustration, in the German published patent applications 35 29 026 and 37 20 624 to arrange the image-recording chip in a "reclining" manner, i.e. parallel to the longitudinal axis of the endoscope.

· Except for this special arrangement of the image-recording chip at the distal end piece of the endoscope, the hitherto proposed "video endoscopes" differ from conventional ones only in that an image conducting system (e.g.,—the relay-lens system), is replaced by an image recorder with an electric transmission system arranged thereafter. The construction of the rest of the endoscope however, (that is, the lens arrangement provided at the distal end, the arrangement of the illumination unit and of the ducts, if any, provided for the tweezers, scissors, and the like) remains practically unchanged. Such devices yield no new examination or treatment possibilities.

Furthermore, the significance of this simple replacing of an image-forwarding system with an image recorder in the state of the art is that the overall lumen of the endoscope, i.e. the required cross-section area, continues to be essentially determined by the "addition" of various lumens, which are needed for the unaltered built-in lens, the ducts for the rinse fluids, tweezers, scissors, etc.

The object of the present invention is to design an endoscope having a video device arranged at the distal end thereof in such a manner that new examination and treatment possibilities are yielded and that, in particular, the overall lumen of the endoscope is no longer determined by the addition of various, single lumens needed for the individual components, such as lens, rinse and manipulation ducts, illumination device, etc.

The present invention is based on the fundamental concept that there are substantially more design possibilities by employing an image-recorder arranged at the distal end of an endoscope than with conventional endoscopes with "fixed", integrated image-giving systems, regardless whether they are provided with a video device or an image-forwarder for transmitting the image from the distal end to the proximal end.

The above object is achieved in accordance with the present invention by combining the lens and the image recorder in a video unit, which is connected to the endoscope shaft in such a moveable manner that the outer contour of the cross-section of the video unit lies essentially within the outer contour of the cross-section of the distal end of the endoscope shaft when introduced into the cavity to be examined following termination of the introduction procedure, the video unit is flexible in relation to the distal end of the endoscope shaft to such an extent that the contour of the cross-section and/or longitudinal section of the video unit is moved beyond the corresponding outer contour of the endoscope shaft.

In other words, the overall inventive concept consists of no longer designing the distal video-examination system as parts fixedly connected to the endoscope and integrated in the endoscope structure, as is the case in the state of the art, but rather to combine the lens and the image recorder and, if need be, the illumination unit for the object field of the lens into a video unit, which is moveable as a whole in relation to the distal end of the endoscope shaft after being introduced into the cavity to be examined.

This fundamental concept of the present invention can be realized in a so-called rigid endoscope as well as in a flexible endoscope. The invented design results in a video-endoscope, which has a number of advantages compared to prior art endoscopes having a video device arranged in a "rigid" manner at the distal end thereof, i.e. fixedly integrated in the structure of the endoscope, or the endoscope shaft:

According to an illustrative embodiment hereto, according to which the video unit can be swung about an axis, which is parallel to the axis of the shaft of the endoscope and eccentric in relation to the front face of the video unit. The video unit can be "swung out" of the endoscope shaft, or in the case of an arrangement "before the shaft", out of the "cross-section contour" of the endoscope shaft. This permits not only examination of the cavity under a different angle of vision, but rather especially in an endoscope with at least one main duct for rinsing fluids, instruments, etc. has the advantage of improved utilization of the available lumen so that the individual lumens, i.e. the cross-section areas of the individual components combined are larger than the entire cross-section area of the endoscope during introduction into the cavity:

For this purpose (by way of illustration), the video unit is arranged during introduction into and withdrawal from the cavity in such a manner that it at least partially covers the duct opening. Following introduction into the cavity, the video unit is brought into the examination position, in which it clears the main duct. In this manner, the cross-section of the endoscope is no longer dictated by addition of the required cross-section areas for the duct or ducts and the cross-section area of the lens including the video unit, but rather only by the largest lumen of the various single lumens. This advantage is also yielded by other embodiments, which are described in more detail in the following section.

In another embodiment the outer diameter of the cross-section of the video unit is almost as large as that of the endoscope shaft. This permits a comparatively large video unit and thereby the use of a large and therefore a fast lens, including the use of an image recorder, (such as, a solid image convertor with a large light-sensitive surface). without the diameter of the endoscope becoming unacceptably large during the introduction and withdrawal phase.

The swinging movement of the video unit moveably joined at the distal end of the endoscope can be carried out in various ways, such as by micro-mechanical actuators, by axes running from the distal to the proximal end, etc. In a preferred embodiment, a pulling cable running from the proximal end to the distal end and back is provided for executing the swinging movement according to claim 4 hereto. This embodiment has the advantage that the pulling cable can be easily run into the "unused" areas of the cross-section of the shaft.

The endoscope may be provided with (at least) one transmission duct, in which elements generating the swinging movement of the video unit, such as the previously mentioned (axes also referred to as moving elements hereinafter), including, if need be, the transmission system for the video signals, are conducted from the distal to the proximal end.

It is preferable if the transmission duct is connected to the main duct by a slit running in the direction of the axis of the endoscope shaft, which permits removal of the transmission system from the transmission duct and thereby a separation of the video unit from the actual endoscope. Also, when the outer contour of the cross-section of the video unit is adapted to the inner contour of the main duct, such a connecting slit facilities pushing the video unit forward from the proximal to the distal end, or pushing the unit back. In this way, the video unit can, by way of illustration, be replaced with another video unit having, for example, a different focal length and therefore a different field of vision, or with a different examination or treatment system, such as a conventional examination optics having a lens and image conveyor, without needing to remove the endoscope shaft from the cavity.

Because the video according to the invention unit clears at least the largest part of the main duct, an additional conventional examination optics having an image conveying system can also be utilized in the main duct.

In any case, it is preferable if the transmission duct also serves as a conductor for the element or elements which generate the motion of the video unit.

Naturally, the moving element may also be arranged in the main duct. This arrangement is particularly advantageous is a thrust rod serving as a moving element is attached to the video unit eccentrically in relation to the cross-section of the video unit. This embodiment has the advantage that after pushing the video unit forward beyond the distal end of the shaft, the video unit is brought into a position, in which it clears the greater part of the cross-section of the duct solely by gravity without requiring additional measures.

In a further embodiment of the invention, the contour of the longitudinal section of the video unit is designed in such a manner that there is an edgeless, smooth transition from the maximum cross-section of the video unit to the cross-section of the thrust rod, which ensures that the video unit can be drawn back into the main duct by simply pulling back the thrust rod thereby permitting easy withdrawal of the endoscope.

In any case, to achieve to optimum exploitation of the available lumen it is advantageous if the moving element, such as the axis or the thrust rod, is hollow and the transmission system is run in the moving element. The moving element may in this event depending on the design of the endoscope (rigid or flexible) be a rigid hollow pipe or a flexible axle. Furthermore, the required "pulling cables" may be provided with an additional function even in conventional, flexible endoscopes so that, by way of illustration, swinging occurs by additionally turning these "pulling cables". Moreover, a transparent plastic cylinder, which simultaneously serves as the light conductor for the illumination light, may be utilized as the element for transmitting the swinging movement. In a further embodiment, in the home position, i.e. in the position in which the endoscope can be introduced into or withdrawn from the cavity, the video unit can be swung completely into the shaft, thus providing optimal protection from damage.

The fundamental concept of the present invention to at least combine the lens and the image recorder into a compact unit, which can be swung "out of the endoscope shaft" following introduction into the cavity, moreover, permits providing not only one swingable unit, but rather several swingable units, of which at least one is a video unit.

It is preferred if the moveable and, in particular, the swingable units are arranged in a row at the endoscope shaft at least in the "swung-in position", as in that case the available lumen is optimally utilized for introduction and the withdrawal procedures. Furthermore, it is also an advantage if the units are arranged in a plane which is perpendicular to the longitudinal axis of the endoscope, following being swung out. This may, by way of illustration, be realized by all the units being initially arranged in a row and being "swung into the endoscope shaft". After swinging out the units, those units which are arranged behind the front most unit are pushed forward into their respective, allocated transmission ducts by shifting of their moving elements until they are in the same plane as the front most unit. Accordingly, the front units may also be correspondingly drawn back.

Employing video units for all the units permits stereo examination with a relatively large stereo base. Accordingly it would also be possible to perform a more extensive, redundant depth analysis of the cavity to be examined with more than two video units.

Moreover, only one unit may be a video unit and the other may be provided with a light emitter. In this manner, by way of illustration, triangulation measuring can be realized.

Furthermore, in addition to the video unit another image giving recorder may be used, by way of illustration, an ultrasonic image recorder.

The fundamental concept of the present invention to combine the lens and the image recorder including, if need be, the illumination unit into a compact video unit permits not only swinging this video unit, but also moving the video unit in relation to the distal end of the endoscope shaft.

This movement can be oblique, diagonal to the endoscope axis or in the direction of the endoscope axis. In particular, a telescopically designed moving element may be provided which permits moving the video unit in relation to the distal end after completing the introduction and drawing back procedures of the unit prior to beginning the withdrawal procedure. This telescopic moving element may be run in the main duct or in the transmission duct of the shaft.

The fundamental concept of the present invention to create a compact video unit, which is not structurally integrated in the endoscope shaft, moreover, permits detaching the video unit from the distal end of the endoscope shaft. In this event, the video unit is only connected to the proximal supply unit via the transmission system in such a manner that it can be employed as a video probe in the cavity.

In this case, it is an advantage if the video unit designed as a video probe can be reattached to the endoscope shaft prior to beginning the withdrawal procedure. Furthermore, it is preferred if the video probe can be moved forward out of the endoscope shaft (claim 25). A suitable design of the "proximal end part" of the video probe even permits removing the latter from the hollow organ without an instrument solely by simply "pulling it out".

Another possible movement of the video unit in accordance with the present invention, within the overall inventive concept, is a rotation or a swinging, of the unit about at least one axis, which is perpendicular to the axis of the endoscope shaft. By this means, by way of illustration, a video unit, which was "initially lying along the shaft", can be "emplaced" following introduction into the cavity.

Furthermore, images of an object to be examined can be taken from different angles of vision. The different possible movements set forth in the claims may be employed singly or in combination: thus the video unit can, by way of illustration, first be swung out of the endoscope shaft about an axis, which is parallel to the axis of the endoscope and eccentric in relation to the front face of video unit, and subsequently moved in the direction of the endoscope shaft by a telescopically designed moving element. Moreover, moving obliquely or diagonally to the axis as well as swinging the video unit about an axis, which is perpendicular to the axis of the endoscope, is also contemplated foreseen. Naturally, these movements can be realized not only by mechanical means. The motions may also be realized with suitably designed drive elements, by way of illustration, micromechanically produced motors, etc.

The video device, which in accordance with the present invention is set up as a unit separated from the actual endoscope, may be set up in the known manner. In particular, the image recorders may be arranged perpendicular to the axis of the endoscope shaft and parallel to the axis of the endoscope shaft. Furthermore, two image recorder with respective lenses or one image recorders with two lenses, the image of which can be selectively aimed at the image recorder, may also be provided. This embodiment permits, by way of illustration, with a 180° lens arrangement, examining a substantially larger object field than is possible with a conventional lens. So-called straight-vision lenses and so-called oblique-vision lenses may also be used.

As a substantially larger lumen is available for the video unit during the introduction and withdrawal procedures due to the fundamental concept of the present invention than is the case with conventional video endoscopes, an image convertor may, moreover, be provided for each color take, i.e. for each primary color, with a dichroic deflection system dividing the image of the lens correspondingly.

Furthermore, the output signals of the image-recorder chip may naturally be transmitted "wirelessly" to the proximal end. Preferable, however, with regard to the size of the construction, the transmission system is realized with connection lines for the electric and/or optical transmission of energy and signals. The individual lines may preferably be combined to a single connection line which may be employed to push the probe forward via the endoscope shaft and to draw back the probe.

The light exit area of the illumination unit may either be arranged "fixedly" to the endoscope shaft or to the video unit.

The fundamental concept of the present invention, moreover, allows greater freedom in the design of the illumination unit. Thus one or several miniature filament lamps, strobe lamps, light diodes and/or semiconductor lasers may be provided in the video unit. Naturally, however the illumination light source may also be arranged proximally in the conventional manner and the light of the illumination light source may be conducted by means of light conductors to the light exit area, where it then emerges. The light conductors may be conventional fiber bundles, or rigid rods, which simultaneously serve as moving elements.

The energy supply of the image recorder and, if need be, of the illumination light source, may be realized by providing opto-electric and/or electro-magnetic transducers in the video unit, which convert the optical or high-frequency electric, respectively inductively coupled-in energy into electric energy suited for the image recorder. In reverse, the output signal of the video unit can also be translated by an electro-optical signal convertor into an optical signal and this signal can be transmitted to the proximal end.

In a further embodiment of the invention, the end area of the video unit facing the proximal end tapers and the distal end area of the endoscope shaft is designed to compliment it. This arrangement permits sure "self-centering" utilization of the video unit or video probe, in the endoscope shaft in the version in which the video unit can be moved beyond the distal end area prior to beginning the withdrawal procedure, particularly a withdrawal of the video probe without it previously having been provided on the endoscope shaft.

In yet another embodiment, chambers which can be filled with fluid, are provided, which upon filling stiffen the endoscope against lateral forces, thus making the flexible endoscope shaft sufficiently rigid that the element can be moved transversely to the endoscope shaft. Moreover, partial filling of the chambers results in the endoscope shaft bending.

The video unit may be separated from the endoscope shaft. In addition, by means of an element which can be magnetically influenced, the video probe may be positioned independently of the endoscope shaft, for example, from outside the body.

Because connection lines have plugs, the cross-section of which is smaller than or the same size as the connection cord, which for its part is substantially smaller than the maximum cross-section of the video unit, the video unit may be separated from the shaft by just pulling out the connection line.

If need be, the video unit can also have a rinsing duct, which by way of illustration can be employed for cleaning the front lens of the objective.

The cross-section of the endoscope shaft may, of course, be round like prior art shafts, whereby the cross-section of the video unit may be round but does not have to be. However, the cross-section of the shaft and the video unit may be designed in the same manner, not round, but rather by way of illustration oval. Clearing the ducts, (for example, tweezer ducts) provided in the shaft can occur by turning the video unit 90° in relation to the shaft.

Other objects, advantages and novel features of the present invention will become apparent from the following detailed description of the invention when considered in conjunction with the accompanying drawings.

DETAILED DESCRIPTION OF THE DRAWINGS

FIG. 1 shows a first preferred embodiment of the present invention, in which a video unit 1 can be swung about an axis 3, which is parallel to the axis 2' of the endoscope shaft 2, shown by way of example as a rigid shaft. The endoscope shaft is provided in a known manner with a main duct 4, which by way of illustration can be used for rinsing with rinsing fluids or into which instruments such as scissors, tweezers, etc. can be inserted. The main duct 4 connects the distal end depicted in FIG. 1, i.e. the end of the shaft 2, which can be inserted into the cavity to be examined, to the proximal end-(not shown), i.e. the end remaining outside of the cavity.

Figure 1A:
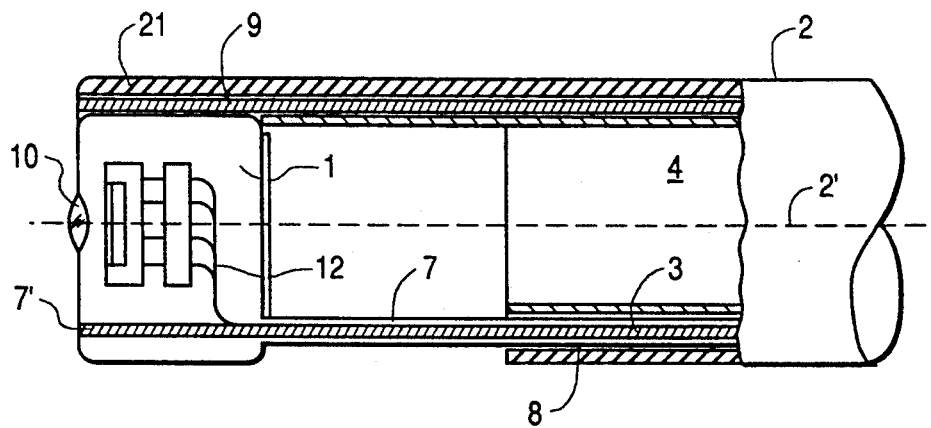
FIGS. 1a and 1b show a longitudinal section through a first preferred embodiment of this invention.
Figure 1B:
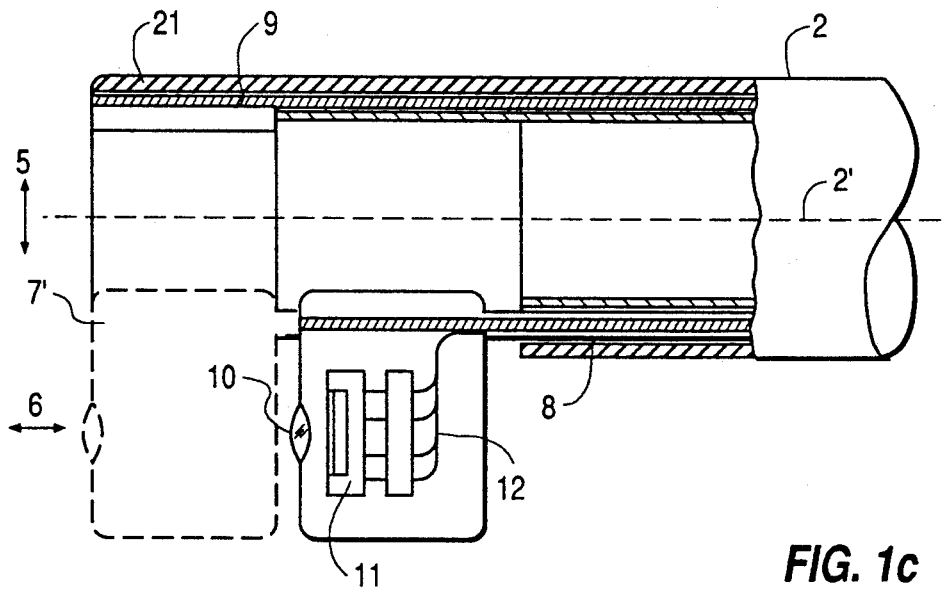

As the axis of rotation 3 of the video unit 1 is arranged eccentrically in relation to the front face of the video unit, the video unit can be swung from the position depicted in FIG. 1a, in which it is swung into the main duct 4 of the endoscope shaft, in the direction of the arrow 5 into a position, in which it completely clears the main duct 4 (FIG. 1b). The dimensions of the video unit 1 and of the shaft and the arrangement of the axis of rotation 3 are selected in such a manner that the outer contour of the video unit lies completely within the outer contour of the shaft when the former is in a swung-in state during examination in the direction of the longitudinal axis. The "outer contour of the cross-section" of the video unit does not extend beyond the corresponding contour of the shaft until after a rotation of the video unit about the axis of rotation 3. In addition the video unit 1 can be moved along an arrow 6, i.e. parallel to the axis 2', permitting not only an alteration of the object field of the video unit, but also the insertion of instruments, such as tweezers, scissors in the main duct 4, which can be bent to a very great degree at the distal end without the bending being hindered by the video unit. Naturally, conventional endoscope optics with a lens and an image transmission system may be used as an additional examination system in the main duct 4.

In order to realize the rotation and the movement, an element 7 is attached to the video unit, the element being run in a transmission duct 8, which is provided on the outer circumference of shaft 2. In the embodiment depicted in FIGS. 1a to 1c, the movement-transmitting element 7 (moving element) is a light conducting rod made of a transparent material. This transparent light conducting rod terminates at a light exit surface 7' at the front side of the video unit 1. In addition, further light conductors 9, which are "rigidly" integrated in the structure of the shaft and which by way of illustration may be conventional fiber bundles, are provided in the illustrated embodiment.

Figure 1C:
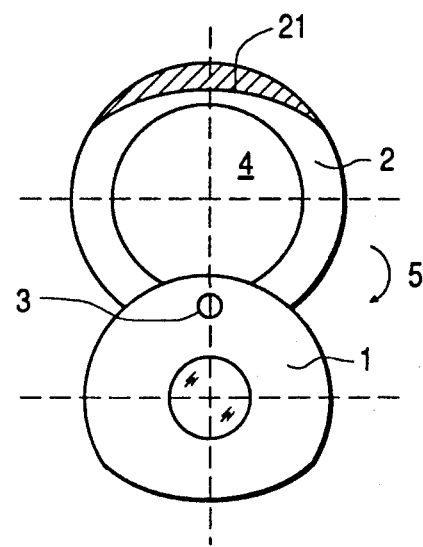
FIG. 1c a top view of the preferred embodiment of FIGS. 1a and 1b.
Figure 1D:
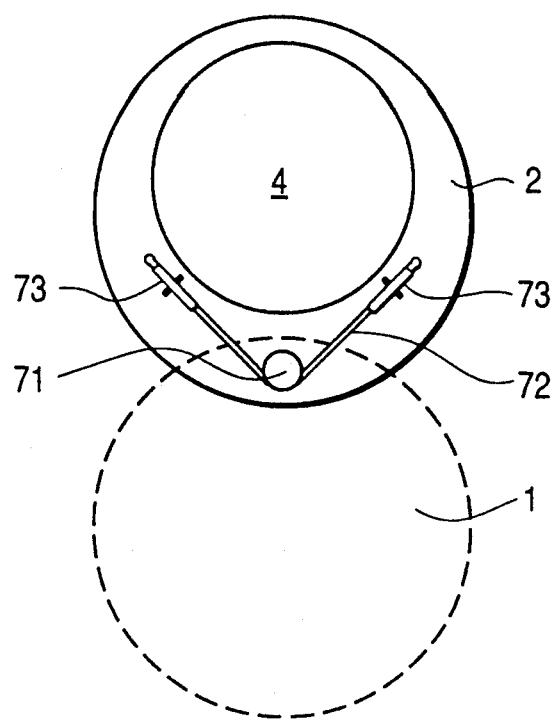
FIGS. 1d and 1e depict the moving elements performing the swinging movement.
Figure 1E:
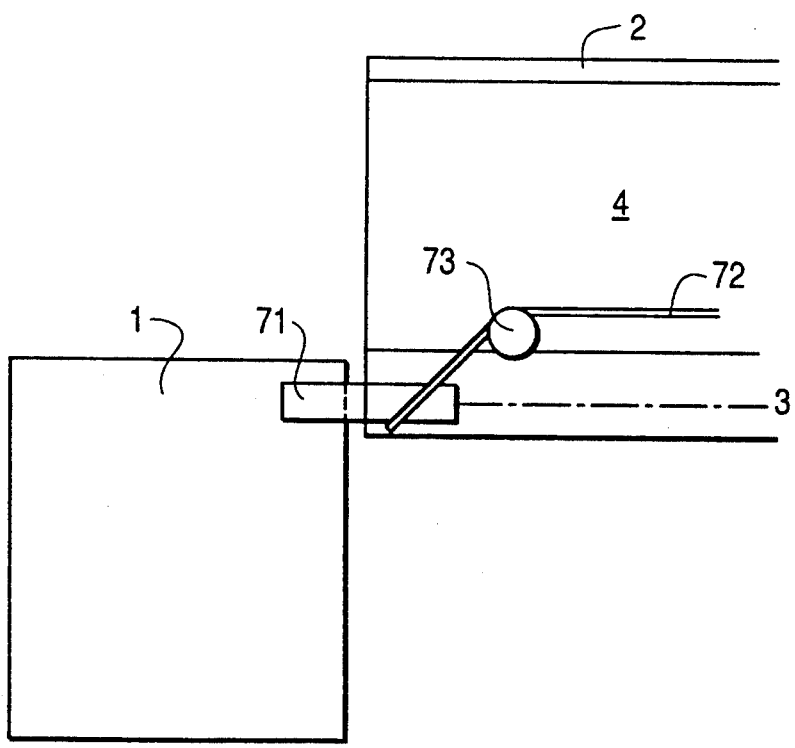

FIGS. 1d and 1e show another preferred embodiment of the rotation movement transmitting element 7. The video unit 1 is moveably joined to the shaft 2 by means of a shaft 71 in such a manner that it can be swung about the axis 3. A pulling line 72 running from the proximal end to the distal end of the shaft 2 and back is provided for turning shaft 71, with two rollers 73 arranged at both sides of the shaft 71 turning the pulling line. Thus moving pulling line 72 by a actuating element (not shown) arranged at the proximal end results in turning the video unit about the axis 3.

The video unit 1 is provided with a lens 10 image recorder chip 11 (both schematically depicted in FIGS. 1a to 1c). The image recorder chip 11 is connectd to a supply unit arranged at the proximal end via the connection lines 12. In the preferred embodiment depicted in FIGS. 1a to 1c, the connection lines 12 are wound about the rod 7. However, the moving element 7 may, naturally, also be designed as a hollow pipe, in which the lines 12 and, if need be, light conducting fibers are run.

In the preferred embodiment depicted in FIGS. 1a to 1c, the video unit 1 with the lens 10 and the image recorder 11 provided therein as well as the light exit area 7' of an illumination unit can be swung out of a position, in which the video unit is essentially arranged at the side of the endoscope shaft 2, into the endoscope shaft 2, which is provided for this purpose with a corresponding projection 21, which is depicted dark in FIG. 1c.

Naturally, the video unit may however be also be arranged before the endoscope shaft 2 and accordingly swung before the endoscope shaft 2. This is shown in a representation corresponding to FIG. 1a in FIG. 2, in which moreover the same designations are used for the same elements as in FIG. 1 thus obviating another description.

Figure 2:
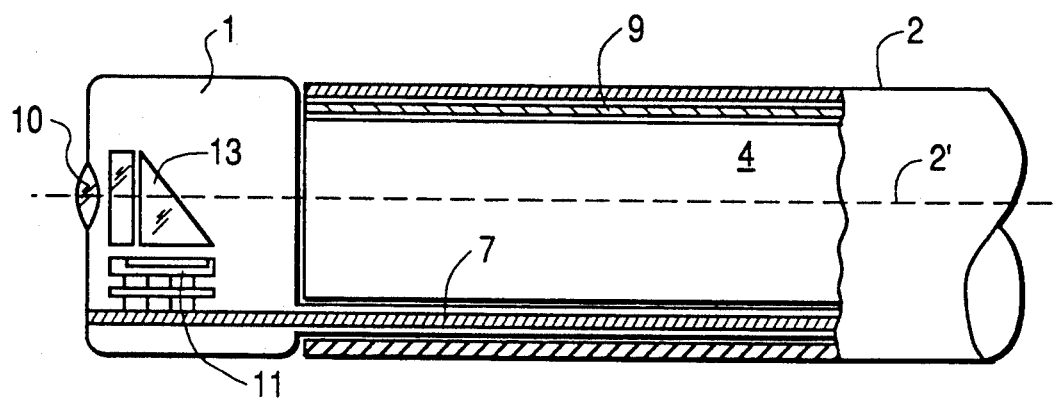
FIG. 2 is a longitudinal section through a second preferred embodiment of the invention.

The preferred embodiment depicted in FIG. 2 also differs from the preferred embodiment illustrated in FIG. 1 in that the image recorder 11 is not arranged perpendicular to the longitudinal axis 2' of the endoscope, but rather parallel thereto. Correspondingly a deflection prism 13 is provided, which deflects the image of the lens 10, which, without the intention of limiting the scope and spirit of the present invention, is a so-called "straight-vision lens" in both preferred embodiments, onto the light-sensitive area of the image recorder 11. A so-called oblique-vision lens may, of course, also be employed.

By virtue of the fundamental concept of the present invention to swing the video unit 1 before or in the main duct 4 during introduction and withdrawal of the endoscope, a substantially larger lumen is available for the video unit than in conventional video endoscopes. As a result, not only larger lenses and image convertors can be employed than in conventional video endoscopes, but also a construction, in which three image recorders for the three primary colors, can be provided.

Figure 3:
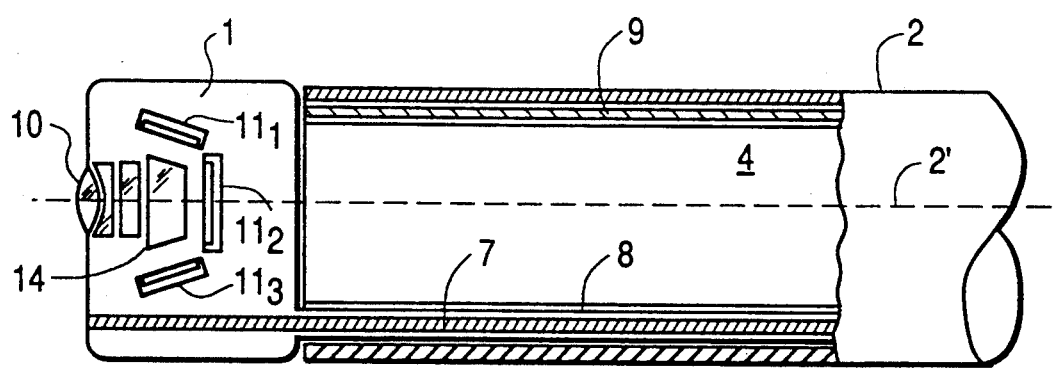
FIG. 3 is a longitudinal section through a third preferred embodiment.

FIG. 3 shows a corresponding preferred embodiment with the three image convertors $11_1$ to $11_3$. A dichroic image element 14 divides the light of the lens 10 into the three image convertors $11_1$ to $11_3$. Other than that, the third preferred embodiment depicted in FIG. 3 corresponds to the preferred embodiment shown in FIG. 2.

Figure 4:
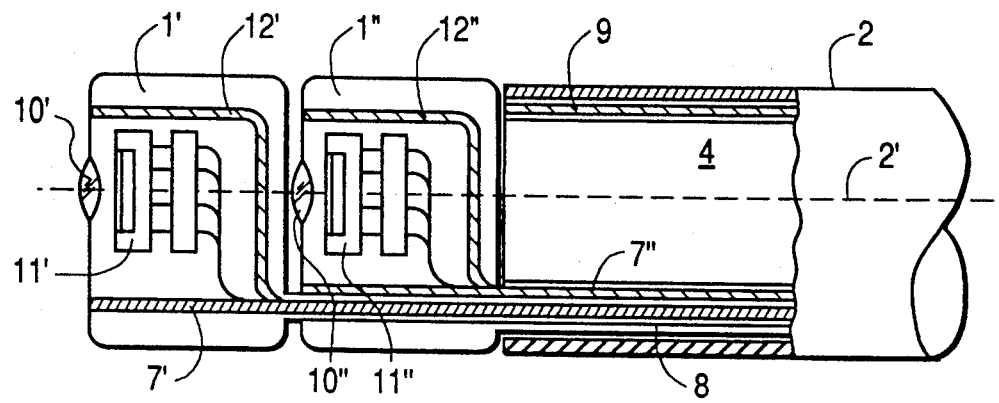
FIG. 4 is a longitudinal section through a fourth preferred embodiment.

In the preferred embodiments described in connection with FIGS. 1 to 3, only one video unit 1 is provided, which accommodates the lens 10, the image recorder 11 and, if need be, the light exit area 7' of an illumination unit, and which is moveable following introduction into the cavity as a whole in relation to the distal end of the endoscope shaft 2. Naturally, more than one video unit can also be provided:

FIG. 4 shows a fourth preferred embodiment, in which the two video units 1' and 1" are provided, the moving elements 7' and 7" of which are run coaxially in a transmission duct 8. Other than that, the elements depicted in FIG. 4 with the same designations as in the previous figures correspond to the elements described, thus obviating another description.

Figure 5A:
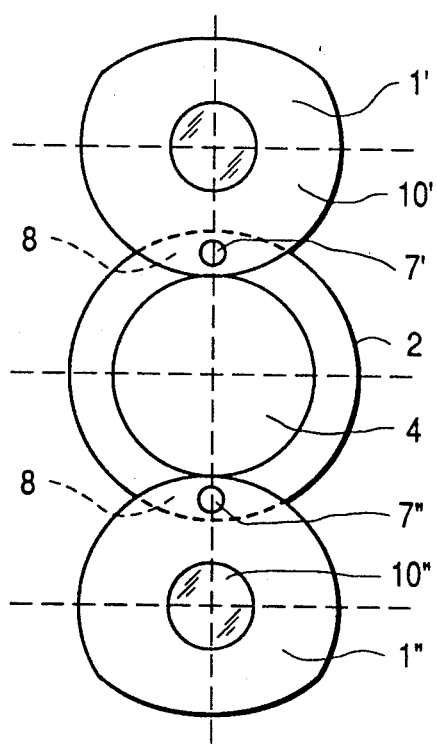
FIGS. 5a and 5b show a top view of two versions of a fifth preferred embodiment.

However, the moving elements 7 for the individual video units can, of course, also be run not coaxially but—as shown in a top view in FIG. 5—in different ducts 8' and 8". If at least one of the two video units 1 or 1' is designed in such a manner that it can be moved in the direction of the longitudinal axis of the endoscope shaft, after swinging out the two video units 1' and 1" can be arranged in the same plane perpendicular to the longitudinal axis of the endoscope. In this manner, by way of illustration, a stereoscopic image is possible.

Figure 5B:
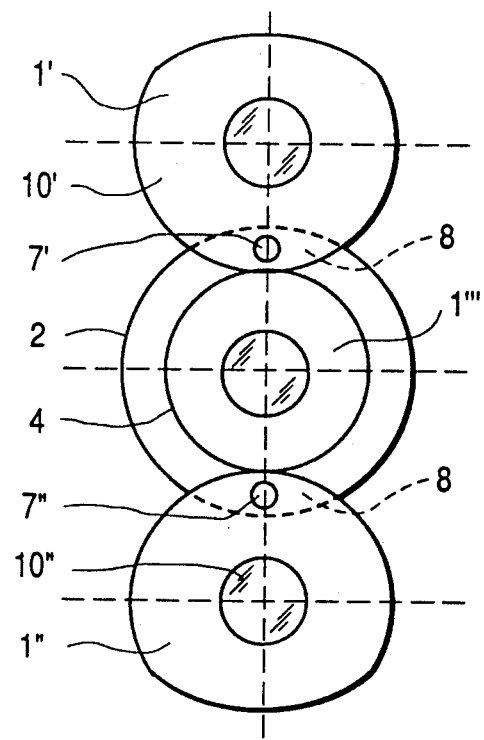

Naturally, in the preferred embodiments shown in FIGS. 4 and 5 it is not necessary that both units are video units. By way of illustration, one of the two units 1', or 1", may accommodate a light source as, by way of illustration, a miniature light bulb, a light diode or a laser diode. Furthermore, one of the units may also accommodate another image giving recorder, as by way of illustration, an ultrasound array. Finally, another endoscopic measuring system, such as two laser diodes, may be integrated in units 1' and 1" and the examination may be conducted with an examination unit, a conventional optical system 1'" or a video unit, introduced into the central main duct 4 (FIG. 5b).

In the preferred embodiments shown in FIGS. 1 to 5, the video unit 1 can be swung about an axis 3, which is parallel to the axis 2' of the endoscope shaft 2 and eccentric in relation to the front area of the video unit 1. In addition, if need be, a movement in the direction of the axis 3 may occur.

Figure 6A:
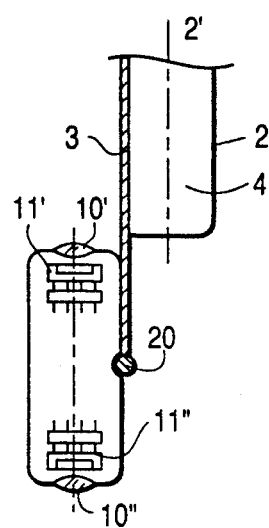
FIGS. 6a to 6c show a sixth preferred embodiment in various positions.
Figure 6B:
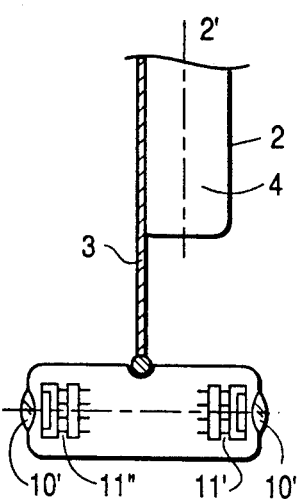
Figure 6C:
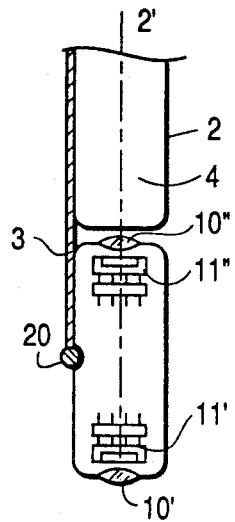

FIGS. 6a to 6c depict a sixth preferred embodiment of the present invention, in which the video unit 1 can be swung about an axis 20, which is perpendicular to the axis 2' of the endoscope shaft 2. Furthermore, in this preferred embodiment, the video unit 1 is provided with two lenses 10' and 10", the optical axes of which enclose a 180° angle, as well as two image recorders 11' and 11".

In the "0° position" shown in FIG. 6a the video unit 1 is folded before the endoscope shaft 2, whereas in the 180° position shown FIG. 6c it lies parallel to the endoscope shaft 2 and, by way of illustration, clears the opening of a duct 4, which is not shown in more detail, in the endoscope shaft. FIG. 6b shows corespondingly the 90° position, in which an examination of the lateral area, such as of an operation area, is possible.

In addition, the video unit may also be swung about an axis 3, which is parallel to the axis 2', according to the preferred embodiments shown in FIGS. 1 to 5.

Figure 7:
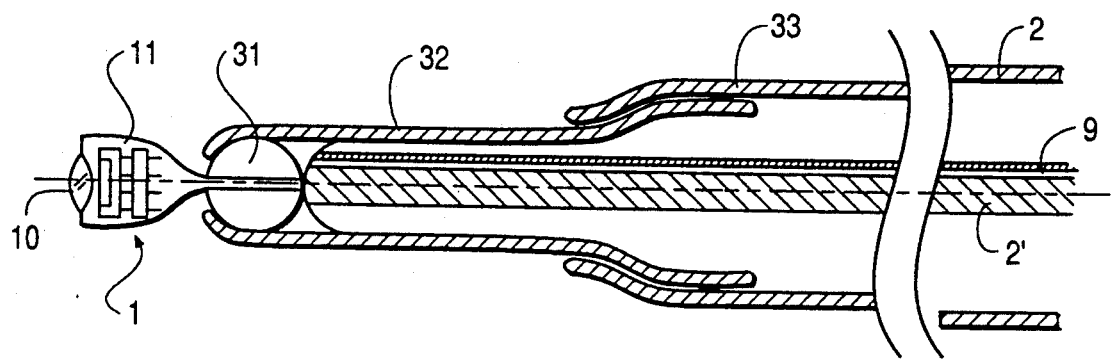
FIG. 7 is a longitudinal section through a seventh preferred embodiment.

FIG. 7 depicts a seventh preferred embodiment, in which the video unit 1 is attached via a ball-and-socket joint 31 to a telescope carrier formed by one of the two elements 32 and 33. The telescope carrier for its part is again moveably joined to the distal end of endoscope shaft 2. By means of this embodiment version, video unit 1 can be pushed forward beyond the distal end of the endoscope shaft 2, thereby permitting more extensive examination. Moreover, the ball-and-socket joint 31 provided at the front end of the telescope, permits examination under different angles of vision.

All the above described preferred embodiments have in common that the video unit 1 remains connected via suitable elements to the endoscope shaft 2 during movement.

Naturally, the video unit 1 may also be designed in such a manner that in a certain position it can be separated from the endoscope shaft 2 or that it may be freely inserted into the duct 4, with the connection to the proximal end being retained by a thrust element.

Figure 8:
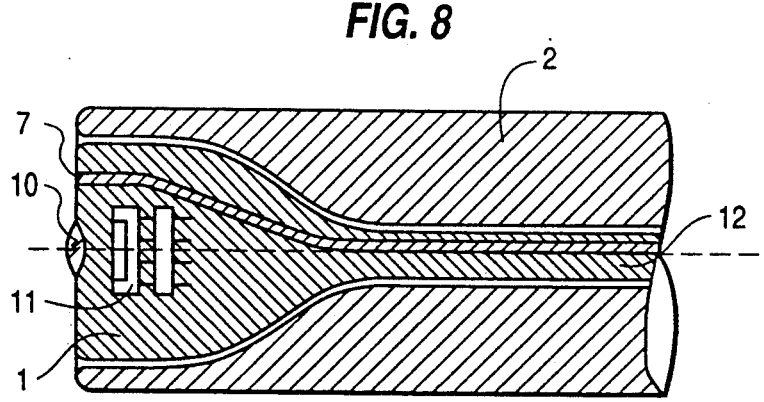
FIG. 8 is a longitudinal section through an eigth preferred embodiment.

FIG. 8 shows schematically a preferred embodiment, in which the video unit 1 is connected to the endoscope shaft only via a connection line 12 and can be moved by it over the distal end of the shaft in such a manner that the video unit can be employed as a video probe. If the proximal end of the video unit 1 and the distal end of the endoscope shaft 2 are designed in a complimentary manner, the video probe (video unit 1) after having been drawn back by means of the line 12, can be easily inserted into the corresponding recess in the endoscope shaft 2 once more.

Figure 9A:
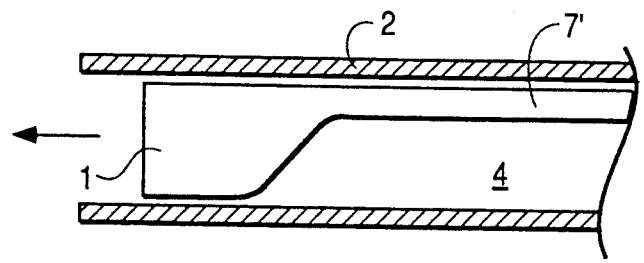
FIGS. 9a and 9b show a longitudinal section through a ninth preferred embodiment in two positions.
Figure 9B:
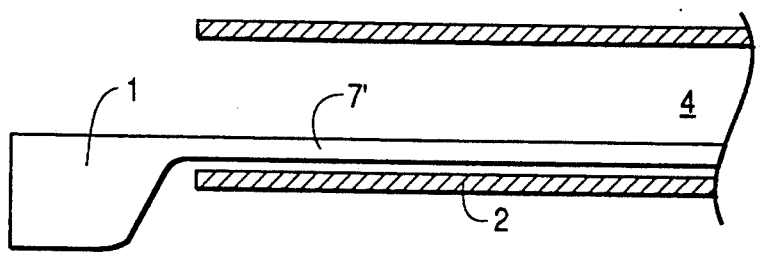

FIGS. 9a and 9b show a preferred embodiment, in which the video unit 1 is only inserted in the main duct 4 of shaft 2 in such a manner that the video unit can be moved therein. A thrust rod 7', which is eccentric in relation to the cross-section of the video unit and which is also arranged in the main duct 4, is provided at the video unit 1. This version has the advantage that after the video unit has been moved beyond the distal end, the video unit is brought into a position, in which it clears the largest part of the cross-section of the duct, without further measures, solely due to gravity (FIG. 9b). In the illustrated preferred embodiment, the contour of the longitudinal section of the video unit 1 is designed to provide an edgeless, smooth transistion from the maximum cross-section of the video unit 1 to the cross-section of the thrust rod 7'. In this way, it is ensured that by simply drawing back the thrust rod, the video unit can be drawn back into the main duct so that in the position depicted in FIG. 9a, in which the video unit 1 is arranged in the main duct 4, easy withdrawal of the endoscope is possible.

In the previous section, the present invention has been described using preferred embodiments without the intention of limiting the scope and spirit of the present invention, within which the most varied and different modifications are possible.

Although the invention has been described and illustrated in detail, it is to be clearly understood that the same is by way of illustration and example, and is not to be taken by way of limitation. The spirit and scope of the present invention are to be limited only by the terms of the appended claims.

In particular, the different possible movements described in the preferred embodiments can be combined with each other:

Thus, a telescopic moving element, at the end of which the video unit is joined in such a manner that it can be swung about an axis, which is parallel to the axis of the endoscope shaft 2, and rotated about an axis, which is perpendicular thereto, may be provided in the transmission duct 8. Furthermore, a possible means of moving the video unit in one or several directions may be provided, which enclose an angle unequal to 0° with the axis of the endoscope shaft, thus to provide an "oblique movement". Furthermore, the endoscope shaft may be designed in such a manner that it can be folded open or it may be provided with a slit so that the video unit can be withdrawn from the shaft together with the connection line attached thereto. For this purpose, a slit may also be provided between the main duct 4 and the transmission duct 8. The afore-described possibilities, of course, may also be employed to the same degree in rigid and flexible endoscopes. In flexible endoscopes it may be necessary "to stiffen" the endoscopes by means of fluid chambers, which can be so that they become semi-flexible in order to realize the various possible movements.

Furthermore, it may be an advantage to compensate the distal turning in the video representation unit arranged at the proximal end by means of prior art image processing methods so that, by way of illustration, "up" and "down" are not reversed for the observer when the unit is swung. If need be, mechanical compensation by turning the image recorder may also occur.

What is claimed is:

1. An endoscope comprising an elongated shaft having a distal end and a proximal end, an illumination unit and a video unit arranged at the distal end of said shaft and connected by a transmission system to a supply unit arranged at the proximal end of said shaft, said video unit comprising a lens adapted to acquire images of an object field illuminated by said illumination unit and at least one image recorder which is adapted to record and transmit images acquired by said lens, said video unit being movable between a first position adjacent the distal end of said shaft, in which an outer contour of a cross section of said video unit lies substantially within an outer contour of a cross section of said distal end of said shaft during introduction and withdrawal of said endoscope into and out of a cavity to be examined, and at least a second position in which the outer contour of the cross section of said video unit lies substantially without the outer contour of a cross section of the distal end of said shaft after completion of the introduction of said endoscope into said cavity, and actuating means for causing said video unit to move between said first position and at least said second position.

2. An endoscope according to claim 1, wherein said video unit is adapted to be rotated about an axis which is parallel to a longitudinal axis of said endoscope shaft and eccentric in relation to the front face of said video unit.

3. An endoscope according to claim 2, wherein the outer diameter of the cross-section of said video unit is nearly as large as that of said endoscope shaft.

4. An endoscope according to claim 2, wherein said video unit is adapted to be rotated by means of a pull cable running from the proximal end to the distal end and back, the pulling of which is guided from axial to lateral via a distal roller system.

5. An endoscope according to claim 1, wherein said endoscope shaft has a main duct which connects the distal end with the proximal end, and said video unit at least partially covers the opening of said duct during the introduction and withdrawal of said shaft into and out of said cavity in said first position, and clears said main duct in said second position.

6. An endoscope according to claim 5, wherein said endoscope shaft has a transmission duct adapted to receive said actuating means and transmission system.

7. An endoscope according to claim 6, wherein said transmission duct is connected to said main duct by a slit running in the direction of a longitudinal axis of said endoscope shaft.

8. An endoscope according to claim 6, wherein said outer contour of the cross-section of said video unit conforms to the inner contour of said main duct in such a manner that the former can be pushed forward through said main duct into an examination position at said distal end of said shaft, and pulled back to the proximal end.

9. An endoscope according to claim 8, wherein said transmission duct is adapted to serve as a guide for said actuating means.

10. An endoscope according to claim 8, wherein said actuating means comprises a thrust rod coupled to said video unit eccentrically in relation to a cross-section of said video unit.

11. An endoscope according to claim 10, wherein a longitudinal contour of said video unit has an edgeless, smooth transition from the maximum cross-section of said video unit to the cross-section of said thrust rod.

12. An endoscope according to claim 11, wherein said thrust rod can be moved within said main duct.

13. An endoscope according to claim 12, wherein said actuating means is hollow, and said transmission system is arranged inside said actuating means.

14. An endoscope according to claim 13, wherein said actuating means is a rigid hollow pipe or a flexible axle.

15. An endoscope according to claim 1, wherein said video unit in said first position is disposed within said shaft.

16. An endoscope according to claim 1, wherein said illumination unit is movable.

17. An endoscope according to claim 16, wherein said illumination and video units are rotatable.

18. An endoscope according to claim 16, wherein said illumination and video units are arranged behind each other along a longitudinal axis of said endoscope shaft.

19. An endoscope according to claim 18, wherein said illumination and video units are adapted to be disposed in a common plane which is perpendicular to the longitudinal axis of said endoscope after being swung out.

20. An endoscope according to claim 19, further comprising a second movable video unit, whereby stereo imaging is possible.

21. An endoscope according to claim 16, further comprising a light transmitter for triangulation measuring.

22. An endoscope according to claim 16, wherein said video unit is provided with another image-giving recorder.

23. An endoscope according to claim 1, wherein said video unit can be moved in a direction which is parallel to a longitudinal axis of said endoscope.

24. An endoscope according to claim 1, wherein said actuating means comprises a telescopically designed moving element adapted to move said video unit along the direction of a longitudinal axis of said endoscope.

25. An endoscope according to claim 1, wherein said video unit can be detached from the distal end of said endoscope shaft, said video unit remaining connected only to the proximal supply unit via said transmission system whereby said video unit is adapted to be used as a video probe, and is adapted to be reattached to the distal end for withdrawal of said endoscope form said cavity.

26. An endoscope according to claim 25, wherein said video unit is adapted to be pushed forward out of said endoscope shaft.

27. An endoscope according to claim 26, wherein said video unit is adapted to be rotated, about at least one axis which is perpendicular to a longitudinal axis of said endoscope shaft.

28. An endoscope according to claim 1, wherein said image recorder is arranged perpendicular to a longitudinal axis of said endoscope shaft in said video unit.

29. An endoscope according to claim 1, wherein said image recorder is arranged parallel to a longitudinal axis of said endoscope shaft in said video unit.

30. An endoscope according to claim 1 wherein said video unit further comprises a second image.

31. An endoscope according to claim 1, wherein said image recorder has two lenses, the image of which can be selectively aimed at said image recorder.

32. An endoscope according to claim 1, wherein said video unit further comprises a plurality of image convertors, onto which a dichroic deflection system steers light from said lens.

33. An endoscope according to claim 1, wherein said transmission system is provided with at least one connection line for electrical and/or optical transmission of energy and signals.

34. An endoscope according to claim 1, wherein electric signal lenses, energy lines and light conductors are combined into a single connection line.

35. An endoscope according to claim 34, wherein said connection line is adapted to control movement of said video unit.

36. An endoscope according to claim 1, wherein a light exit area of the illumination unit is provided at said endoscope shaft.

37. An endoscope according to claim 36, wherein said light exit area of said illumination unit is provided at said video unit.

38. An endoscope according to claim 37, wherein said illumination unit is provided with an illumination light source arranged in said video unit.

39. An endoscope according to claim 37, wherein said illumination unit is provided with an illumination light source arranged at said proximal end, and light conductors adapted to conduct light from said light source to said video unit.

40. An endoscope according to claim 1, wherein said video unit is provided with transducers adapted to supply energy to the image recorder and to said illumination light source, said transducers being one of: opto-electrical and electromagnetic.

41. An endoscope according to claim 1, wherein in said video unit comprises an opto-electrical signal converter for the output signal of said image recorder.

42. An endoscope according to claim 26, wherein an end area of said video unit, which is facing the proximal end of said endoscope shaft has a tapered contour, and the distal end area of said endoscope shaft is designed in a complimentary manner.

43. An endoscope according to claim 42, wherein said endoscope shaft is flexible and is provided with chambers, adapted to be filled with fluid, whereby said endoscope shaft becomes rigid against lateral forces upon being filled.

44. An endoscope according to claim 1, wherein said endoscope shaft is adapted to be folded open along the longitudinal axis thereof so that said video unit can be separated from said endoscope shaft.

45. An endoscope according to claim 1, wherein said endoscope shaft is provided with a longitudinal slit that said video unit can be separated from said endoscope shaft.

46. An endoscope according to claim 1, wherein said video unit comprises a magnetically influenced element for contactless positioning of said video unit independent of said endoscope shaft.

47. An endoscope according to claim 34, wherein said connection line is provided with plugs, the size of a cross-section of which is no greater than a cross section of the connection lines, which are substantially smaller than the maximum size of a transverse cross-section of said video unit.

48. An endoscope according to claims 1, wherein an optical axis of said lens of said video unit is disposed at an angle with the axis of said endoscope shaft.

49. An endoscope according to claim 1, wherein said video unit is provided with at least one rinsing duct to rinse said lens.

50. An endoscope according to claim 1, wherein an examination unit with image forwarders can be utilized instead of said video unit.

51. An endoscope according to claim 50, wherein said examination unit is adapted to be inserted in said main duct.

52. An endoscope according to claim 1, wherein a crosssection of said shaft and a cross section of said video unit are oval and said video unit is adapted to be rotated 90° about a longitudinal axis of said shaft.

* * * * *